(12) United States Patent
Chinta et al.

(10) Patent No.: US 8,450,546 B2
(45) Date of Patent: May 28, 2013

(54) PROCESS FOR THE OXIDATIVE COUPLING OF HYDROCARBONS

(75) Inventors: Sivadinarayana Chinta, Missouri City, TX (US); Joseph Thorman, Houston, TX (US); James Butler, League City, TX (US); Joe Hunter, Friendswood, TX (US); Taylor Rives, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 359 days.

(21) Appl. No.: 12/494,138

(22) Filed: Jun. 29, 2009

(65) Prior Publication Data

US 2010/0331593 A1 Dec. 30, 2010

(51) Int. Cl.
*C07C 2/66* (2006.01)

(52) U.S. Cl.
USPC ............ 585/435; 585/438; 585/452; 585/943

(58) Field of Classification Search
USPC .................................. 585/435, 438, 452, 943
See application file for complete search history.

(56) References Cited

U.S. PATENT DOCUMENTS

| | | | |
|---|---|---|---|
| 4,239,658 A | 12/1980 | Mitchell, III et al. | |
| 4,523,049 A | 6/1985 | Jones et al. | |
| 4,656,144 A | 4/1987 | Hosaka et al. | |
| 4,658,076 A | 4/1987 | Kolts et al. | |
| 4,658,077 A | 4/1987 | Kolts et al. | |
| 4,672,145 A | 6/1987 | Kolts et al. | |
| 4,704,487 A | 11/1987 | Devries et al. | |
| 4,704,493 A | 11/1987 | Devries et al. | |
| 4,774,216 A | 9/1988 | Kolts et al. | |
| 4,775,654 A | 10/1988 | Kolts et al. | |
| 4,826,796 A | 5/1989 | Erekson et al. | |
| 4,895,823 A | 1/1990 | Kolts et al. | |
| 4,950,827 A | 8/1990 | Erekson et al. | |
| 4,950,830 A | 8/1990 | Erekson et al. | |
| 4,950,836 A | 8/1990 | Kimble et al. | |
| 4,956,327 A | 9/1990 | Erekson et al. | |
| 4,962,252 A | 10/1990 | Wade | |
| 4,968,655 A * | 11/1990 | Jezl et al. ...................... | 502/242 |
| 4,982,038 A | 1/1991 | Kimble et al. | |
| 4,996,382 A * | 2/1991 | Matsuura et al. ............. | 585/500 |
| 5,087,787 A | 2/1992 | Kimble et al. | |
| 5,097,086 A | 3/1992 | Lee et al. | |
| 5,105,045 A | 4/1992 | Kimble et al. | |
| 5,118,899 A | 6/1992 | Kimble et al. | |
| 5,132,482 A | 7/1992 | Smith et al. | |
| 5,146,027 A | 9/1992 | Gaffney | |
| 5,157,188 A | 10/1992 | Kolts et al. | |
| 5,160,502 A | 11/1992 | Kimble et al. | |
| 5,210,357 A | 5/1993 | Kolts et al. | |
| 5,406,017 A | 4/1995 | Withers, Jr. | |
| 5,959,170 A | 9/1999 | Withers, Jr. | |
| 6,020,533 A | 2/2000 | Lewis et al. | |
| 6,096,934 A | 8/2000 | Rekoske | |
| 2007/0055083 A1 | 3/2007 | Bagherzadeh et al. | |
| 2008/0281136 A1 | 11/2008 | Bagherzadeh et al. | |

OTHER PUBLICATIONS

Haber, Block and Delmon. "Manual of Methods and Procedures for Catalyst Characterization", Pure & Appl. Chem., vol. 67, Nos. 8/9, pp. 1257-1306 (1995).

Khan and Ruckenstein. "Oxidative Methylation of Toluene with Methane over Superbasic Catalysts: A Selective Route to Styrene and Ethylbenzene through Alternative Feedstocks". Journal of Catalysis 143, pp. 1-21 (1993).

Lunsford, J.H. "The Catalytic Oxidative Coupling of Methane", Angew, Chem. Intl. Ed. Engl. 34, p. 970 (1995).

\* cited by examiner

*Primary Examiner* — Thuan D Dang (57) ABSTRACT

A method for the oxidative coupling of hydrocarbons, such as the oxidative coupling of methane to toluene, includes providing an oxidative catalyst inside a reactor, and carrying out the oxidative coupling reaction under a set of reaction conditions. The oxidative catalyst includes (A) at least one element selected from the group consisting of the Lanthanoid group, Mg, Ca, and the elements of Group 4 of the periodic table (Ti, Zr, and Hf); (B) at least one element selected from the group consisting of the Group 1 elements of Li, Na, K, Rb, Cs, and the elements of Group 3 (including La and Ac) and Groups 5-15 of the periodic table; (C) at least one element selected from the group consisting of the Group 1 elements of Li, Na, K, Rb, Cs, and the elements Ca, Sr, and Ba; and (D) oxygen.

6 Claims, 5 Drawing Sheets

PROCESS FOR THE OXIDATIVE COUPLING OF HYDROCARBONS

CROSS-REFERENCE TO RELATED APPLICATIONS

The present invention is related to co-pending applications titled: Catalysts For Oxidative Coupling Of Hydrocarbons; and Process For The Oxidative Coupling Of Methane, both filed by Fina Technology, Inc. on the same date as the present application.

FIELD

The present invention generally relates to the oxidative coupling of hydrocarbons.

BACKGROUND

Polystyrene is a plastic used in many applications. The plastic can be extruded, injection molded, or blow molded to make objects like plastic cups and utensils, and casings for CDs. Polystyrene can also be formed with a rubber such as polybutadiene to make high impact polystyrene, or HIPS, which is more resistant to impact than normal polystyrene. HIPS can be used in toys, casings for appliances, and containers for food and medical supplies. One of the most recognizable forms of polystyrene is its foamed form, which can be used in packing materials and can be molded into containers, plates, cups and other shapes.

The monomer styrene is commonly produced via the dehydrogenation of ethylbenzene. This reaction can have several drawbacks, one being the formation of side products, such as benzene, toluene, and unreacted ethylbenzene. Another drawback is that ethylbenzene and styrene have similar boiling points, which can make their separation difficult.

Ethylbenzene, in turn, is generally produced via the alkylation of benzene with ethylene. The reaction can create several side products, such as polyalkylated benzene. One significant drawback to this reaction is the relatively expensive reactants that are required. Both ethylene and benzene can be obtained from refined petroleum. Ethylene is obtained predominantly from the thermal cracking of hydrocarbons, such as ethane, propane, butane, or naphtha, and generally goes through several cycles of distillation to obtain a certain purity level. Ethylene from these sources can include a variety of undesired products, including diolefins and acetylene, which can be costly to separate from the ethylene. Thermal cracking and separation technologies for the production of relatively pure ethylene can result in significant production costs.

The costs associated with the production of polystyrene can be considered significant, when such production relies on the alkylation of benzene with ethylene and the dehydrogenation of ethylbenzene for obtaining the monomer styrene. It would be desirable to have alternate methods for the production of ethylbenzene and styrene that is more economical.

SUMMARY

Embodiments of the present invention generally include a method for the oxidative coupling of hydrocarbons, such as the oxidative coupling of methane to toluene. The method can include the steps of preparing oxidative catalysts and running the oxidative coupling reaction inside the reactor over the oxidative catalyst, according to a set of reaction conditions.

An embodiment of the present invention is the preparation and/or use of a catalyst that includes (A) at least one element selected from the group consisting of the Lanthanoid group, Mg, Ca, and the elements of Group 4 of the periodic table (Ti, Zr, and Hf). The catalyst further includes (B) at least one element selected from the group consisting of the Group 1 elements of Li, Na, K, Rb, Cs, and the elements of Group 3 (including La and Ac) and Groups 5-15 of the periodic table and (C) at least one element selected from the group consisting of the Group 1 elements of Li, Na, K, Rb, Cs, and the elements Ca, Sr, and Ba; along with (D) oxygen. If an element from Group 1 of the periodic table is used in (B), it cannot be used in (C). The catalyst can then be dried, calcined, and meshed before being placed in a reactor. The catalyst can be calcined by heating the catalyst to elevated temperatures, such as above 750° C.

The element(s) selected from (A) can range from 40 to 90 wt % of the catalyst. The element(s) selected from (B) can range from 0.01 to 40 wt % of the catalyst. The element(s) selected from (C) can range from 0.01 to 40 wt % of the catalyst. The oxygen in (D) can range from 10 to 45 wt % of the catalyst.

The product distribution of the oxidative coupling reaction can be altered by adjusting the temperature of the reactor. Adjusting the temperature can also alter the exotherm produced by oxidative coupling.

An embodiment of the invention is a method for the oxidative coupling of methane to toluene that includes providing a hydrocarbon feedstream including methane and toluene and providing an oxidative catalyst within a reactor. The catalyst includes (A) at least one element selected from the group consisting of the Lanthanoid group, Mg, Ca, and the elements of Group 4 of the periodic table (Ti, Zr, and Hf) the elements from (A) ranging from 40 to 90 wt % of the catalyst; (B) at least one element selected from the group consisting of the Group 1 elements of Li, Na, K, Rb, Cs, and the elements of Group 3 (including La and Ac) and Groups 5-15 of the periodic table, the elements from (B) ranging from 0.01 to 40 wt % of the catalyst; (C) at least one element selected from the group consisting of the Group 1 elements of Li, Na, K, Rb, Cs, and the elements Ca, Sr, and Ba, the elements from (C) ranging from 0.01 to 40 wt % of the catalyst; and (D) oxygen ranging from 10 to 45 wt % of the catalyst; wherein if an element from Group 1 of the periodic table is used in (B), it cannot be used in (C); wherein the catalyst is calcined after the elements are combined. The hydrocarbon feedstream and an oxygen source are fed to the reactor wherein oxidative coupling of methane to toluene occurs over the oxidative catalyst according to a set of reactions conditions. A product stream that includes styrene and ethylbenzene is recovered from the reactor.

The temperature can be from 500° C. to 800° C., optionally from 550° C. to 700° C. The molar ratio of methane to oxygen can be from 1:1 to 100:1, optionally from 4:1 to 80:1. The molar ratio of methane to toluene can be from 1:1 to 50:1, optionally from 8:1 to 30:1. The catalyst can be pretreated in the reactor before it is used for the oxidative coupling of hydrocarbons, the pretreatment consisting of heating the reactor to above 750° C. under an air flow for at least 1 hour.

The composition of the product hydrocarbons can be adjusted by adjusting the temperature of the reaction. The composition can also be adjusted by adjusting the space velocity of the reaction.

DETAILED DESCRIPTION

The results of oxidative coupling reactions can be influenced by many factors, such as reaction conditions, source and contents of the feed, and reactor design. The catalyst used for the reaction can be one of the most important factors. The effectiveness of the reaction can be measured in terms of conversion, selectivity, and yield. Conversion refers to the percentage of reactant (e.g. methane) that undergoes a chemical reaction. Selectivity refers to the relative activity of a catalyst in reference to a particular compound in a mixture. Selectivity is quantified as the proportion of a particular product relative to all others.

An embodiment of the present invention is a process for the oxidative methylation of toluene (OMT), as well as the oxidative coupling of other hydrocarbons, including the steps of providing a catalyst and running the reactor according to a set of reaction conditions. The process can include steps such as preparing an oxidative catalyst, pretreating the oxidative catalyst inside a reactor, and carrying out the oxidative coupling reaction inside the reactor, according to a set of reaction conditions. Preparation and pretreatment of the catalyst and reaction conditions can influence the conversion, selectivity, and yield of OMT and other coupling reactions.

One aspect of the process of the present invention involves the preparation of a catalyst for OCM. A catalyst of the present invention generally includes a substrate, one or more metal promoters and oxygen. The catalyst can vary in terms of its activity, useful run life, and others characteristics. This variation can be influenced by the selection of the substrate and the combination of metal promoters supported by the substrate.

According to an embodiment, the catalyst of the present invention can include a substrate that ranges from 40 to 90 wt % of the catalyst, the substrate made of one or more of the elements of Set A consisting of: the Lanthanoid group (La, Ce, Pr, Nd, Sm, Eu, Gd, Tb, Dy, Ho, Er, Th, Yb, Lu), Mg, Ca, and the elements of Group 4 of the periodic table (Ti, Zr, and Hf). The substrate supports a first promoter that ranges from 0.01 to 40 wt % of the catalyst chosen from one or more of the elements of Set B consisting of: Li, Na, K, Rb, Cs, and the elements of Group 3 (including La and Ac) and Groups 5-15 of the periodic table. The substrate further supports a second promoter that ranges from 0.01 to 40 wt % of the catalyst chosen from one or more of the elements of Set C consisting of: Li, Na, K, Rb, Cs, Ca, Sr, and Ba. If an element from Group 1 of the periodic table (Li, Na, K, Rb, Cs) is used as a catalytic element from Set B it cannot be used as a catalytic element from Set C. The catalyst further includes Set D, which consists of oxygen, in a range of 10 to 45 wt %. All percentages are for the catalyst after calcination.

The catalyst contains at least one element from each of the Sets A, B, C, and D in the ranges given above. At least 90 wt % of the catalyst is made of the elements of Sets A, B, C and oxygen in the final catalyst composition after a calcination procedure. Optionally at least 95 wt % of the catalyst is made of the elements of Sets A, B, C and D in the final catalyst after a calcination procedure. Residual anions may be present in the final catalyst, e.g. nitrate, halide, sulfate and acetate. The catalyst can vary in terms of its activity, its basicity, its lifetime, and other characteristics. This variation can be influenced by the selection of the elements chosen from Sets A, B, C and D and their respective content in the catalyst.

The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

The term "substrate" is not meant to indicate that this component is necessarily inactive, while the other metals and/or promoters are the active species. On the contrary, the substrate can be an active part of the catalyst. The term "substrate" would merely imply that the substrate makes up a significant quantity, generally 40% or more by weight, of the entire catalyst. The promoters individually can range from 0.01% to 40% by weight of the catalyst, optionally from 0.01% to 10%. If more than one promoters are combined, they together generally can range from 0.01% up to 50% by weight of the catalyst. The elements of the catalyst composition can be provided from any suitable source, such as in its elemental form, as a salt, as a coordination compound, etc.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can be supported by a structured material comprising an alumina or aluminate framework. The content of such a binder material, extrusion aids, structured material, or other additives, and their respective calcination products, will not be taken into consideration within the stated percentage ranges of Sets A-D stated herein. As an additional example a binder material, which can contain elements that are contained within Sets A-D, can be added to the catalyst composition. Upon calcination these elements can be altered, such as through oxidation which would increase the relative content of oxygen within the final catalyst structure. The binder material elements and the calcination products are not taken into consideration within the stated percentage ranges of Sets A-D stated herein. The combination of the catalyst of the present invention combined with additional elements such as a binder, extrusion aid, structured material, or other additives, and their respective calcination products, are included within the scope of the invention.

In one aspect, the invention is a method for the preparation of an oxidative catalyst for OMT, or another oxidative coupling reaction. In one embodiment, the catalyst can be prepared by combining a substrate chosen from at least one element from Set A with at least one promoter element chosen from Set B, at least one promoter element chosen from Set C, and oxygen from Set D. The present invention is not limited by the method of catalyst preparation, and all suitable methods should be considered to fall within the scope herein. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations. In general, any method can be used which provides compositions of matter containing the prescribed components in effective amounts.

According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

In an embodiment, the substrate can be a metal oxide of one or more elements of Set A. One example of an oxide substrate useful for the present invention is magnesium oxide, MgO. The oxide substrate can be either obtained commercially or produced in the lab. For instance, a metal oxide can be made by thermal decomposition of its corresponding salt at elevated temperatures up to 750° C. The choice of precursor salt from which the oxide substrate is produced can have some effect on the performance of the eventual catalyst.

When slurries, precipitates or the like are prepared, they will generally be dried, usually at a temperature sufficient to volatilize the water or other carrier, such as about 100° C. to about 250° C. In all cases, irrespective of how the components are combined and irrespective of the source of the components, the dried composition is generally calcined in the presence of a free oxygen-containing gas, usually at temperatures between about 300° C. and about 900° C. for from 1 to about 24 hours. The calcination can be in a reducing or inert atmosphere or an oxygen-containing atmosphere.

Depending on the catalyst, a pretreatment of the catalyst may, or may not, be necessary. In one embodiment the invention involves the pretreatment of an oxidative catalyst for OMT, or another oxidative coupling reaction. The prepared catalyst can be ground, pressed and sieved and loaded into a reactor. The reactor can be any type known in the art to make catalyst particles, such as a fixed bed, fluidized bed, or swing bed reactor. The reactor set-up can optionally include a recycle stream. Optionally an inert material, such as quartz chips, can be used to support the catalyst bed and to place the catalyst within the bed. For the pretreatment, the reactor can be heated elevated temperatures, such as 800° C. to 900° C. with an air flow, such as 100 mL/min, and held at these conditions for a length of time, such as 1 to 3 hours. Then, the reactor can be cooled down to a temperature of around the operating temperature of the reactor, for example 500° C. to 650° C., or optionally down to atmospheric or other desired temperature. The reactor can be kept under an inert purge, such as under helium.

In another aspect, the invention involves reaction conditions for OMT, or another oxidative coupling reaction. Several parameters including feed composition, molar ratio of hydrocarbon reactant to oxygen, temperature, pressure, time on stream, preparation method, particle size, porosity, surface area, contact time and others can influence the outcome of the reaction. For almost every reaction condition, there can be a range of values best suited to oxidative coupling. Measures are generally taken to increase conversion and selectivity.

Although contaminants that might significantly interfere with the oxidative coupling reaction should be avoided, the addition of trace quantities of a reaction modulator may be useful. Reaction modulators can be used for the control or alteration of conversion, selectivity, or activity of a particular catalyst or in response to certain reaction conditions. Non-limiting examples of possible reaction modulators include chlorine, ethylene and carbon monoxide.

Inert diluents such as helium and nitrogen may be included in the feed to adjust the gas partial pressures. Optionally, $CO_2$ or water (steam) can be included in the feed stream as these components may have beneficial properties, such as in the prevention of coke deposits. The pressure for oxidative coupling reactions can generally range from 1 psia to 200 psia or more. The reaction pressure is not a limiting factor regarding the present invention and any suitable condition is considered to be within the scope of the invention.

The temperature for oxidative coupling reactions can generally range from 500° C. to 800° C., optionally from 600° C. to 750° C. The reaction temperature is not a limiting factor regarding the present invention and any suitable condition is considered to be within the scope of the invention.

Any suitable space velocity can be considered to be within the scope of the invention. As used herein the space velocity shall be defined as: space velocity=[feed flow as vapor ($cm^3$/h)]/[catalyst weight (g)]. A standard reference temperature and pressure (72° F. and 14.7 psia) is used to convert a liquid under these conditions, such as toluene, to a feed vapor flow. For example: 0.076 $cm^3$/min of liquid toluene is converted into moles and then using 22.4 L/mol (as if it were an ideal gas) it is converted into a vapor flow of 16 $cm^3$/min. The space velocity can generally range from 15,000 $cm^3 g^{-1} h^{-1}$ to 100,000 $cm^3 g^{-1} h^{-1}$, optionally from 20,000 $cm^3 g^{-1} h^{-1}$ to 85,000 $cm^3 g^{-1} h^{-1}$. This range is an indication of possible space velocities, such as for a fixed bed reactor. Of course altering the catalyst composition, the amount of inert material, etc can alter the space velocity outside of this range. Also a change in the reactor from a fixed bed to an alternate design, such as a fluidized bed can also dramatically change the relative space velocity and can be outside of the stated range above. The space velocity ranges given are not limiting on the present invention and any suitable condition is considered to be within the scope of the invention.

In the case of OMT, the feed will include toluene along with methane and oxygen. The toluene can be vaporized and introduced to the reactor either by passing the oxygen and methane gas mixture through a toluene vapor saturator right before the inlet of the reactor tube, or by syringe-pumping the liquid toluene into the gas flow and vaporizing it in a preheated zone (250–300° C.) before entering the reactor. The methane to oxygen molar ratio can range from 1:1 to 100:1, optionally from 4:1 to 80:1. The molar ratio of methane to toluene can be from 1:1 to 50:1, optionally from 8:1 to 30:1. Temperature can be from 300° C. to 900° C., optionally from 350° C. to 750° C.

Although methane and toluene are considered the main reactants of OMT, oxygen can be another important component of the feed. Oxygen is a required component of the feed for oxidative coupling. Methane can be obtained from natural gas, or from organic sources, such as the decomposition of waste through fermentation. Whatever the source, methane used in OMT should not contain contaminants that might significantly interfere or give a detrimental effect on the oxidative coupling reaction. The oxygen source can be any source suitable for providing oxygen to the reaction zone such as pure oxygen, oxygen-enriched air, or air. The gas containing oxygen should not contain any contaminants that might significantly interfere with the oxidative coupling reaction. Alternate sources of oxygen may also be used, such as nitrobenzene, nitrous oxide or other oxygen containing compounds.

For the present invention, the methane to oxygen molar ratio can be from 1:1 to 30:1, optionally from 4:1 to 10:1. Oxygen can be fed intermittently, alternating with the hydrocarbon stream or optionally can be fed simultaneously into the reactor with the hydrocarbon reactants.

Products leaving the reactor can be monitored with gas chromatography, or by some other method. Products can be separated using distillation or some other method.

The following examples are intended to give a better understanding of the present invention in its many embodiments, but are not intended to limit the scope of the invention in any way.

COMPARATIVE EXAMPLE A

An oxidative catalyst was prepared comprising a MgO substrate that was promoted with Ba. The Ba/MgO catalyst was used in the oxidative coupling of methane and the oxidative methylation of toluene. The catalyst included 5% Ba by weight and was prepared from barium nitrate (6.53 g) (Sigma Aldrich, 98.0%) and MgO (23.46 g) (Fisher, 99%) by incipient wetness impregnation methodology in aqueous solution. The mixture was dried at 120° C. for 3 h and then calcined at 850° C. in air for 1 h. The catalyst was ground, pressed and sieved to 20-40 mesh size (420-841 µm) and 0.577 g of catalyst was loaded into a quartz reactor using quartz wool plugs and quartz chips to hold the catalyst bed in place. For catalyst pretreatment, the reactor was heated to 850° C. under 100 ml/min of air and held for 2 hours. The reactor was then cooled down to 600° C. under helium to prepare for the OMT experiments.

For the OMT experiments four trials were conducted, at reaction temperatures between 550° C. and 650° C. All reaction conditions other than temperature were held constant during the four trials. The oxygen source was air. The methane to oxygen molar ratio was 5:1. The methane to toluene molar ratio was 15:1. The total flow of gasses was 500 cm$^3$/min (240 cm$^3$/min air, 244 cm$^3$/min methane, 0.076 cm$^3$/min liquid toluene), and the space velocity was 51,993 cm$^3$g$^{-1}$h$^{-1}$. Product samples were taken after twenty minutes of run time and analyzed for product distribution. The results of the trials are shown in the table below.

TABLE 1

Results for OMT over Ba/MgO catalyst

| | Reaction Temperature | | | |
|---|---|---|---|---|
| | 550° C. | 570° C. | 600° C. | 650° C. |
| Toluene Conversion (mol %) | 3.2 | 6.8 | 7.3 | 9.9 |
| Benzene Selectivity (%) | 65.8 | 85.4 | 74.5 | 49.3 |
| Ethylbenzene Selectivity (%) | 3.6 | 5.0 | 5.8 | 7.0 |
| Total Xylene Selectivity (%) | 2.9 | 2.0 | 2.2 | 2.5 |
| Styrene Selectivity (%) | 9.6 | 18.5 | 25.5 | 41.4 |
| Benzaldehyde Selectivity (%) | 29.5 | 1.2 | 0.6 | 0.3 |
| Total Stilbene Selectivity (%) | 0.2 | 0.3 | 0.4 | 0.3 |

Figure 1:
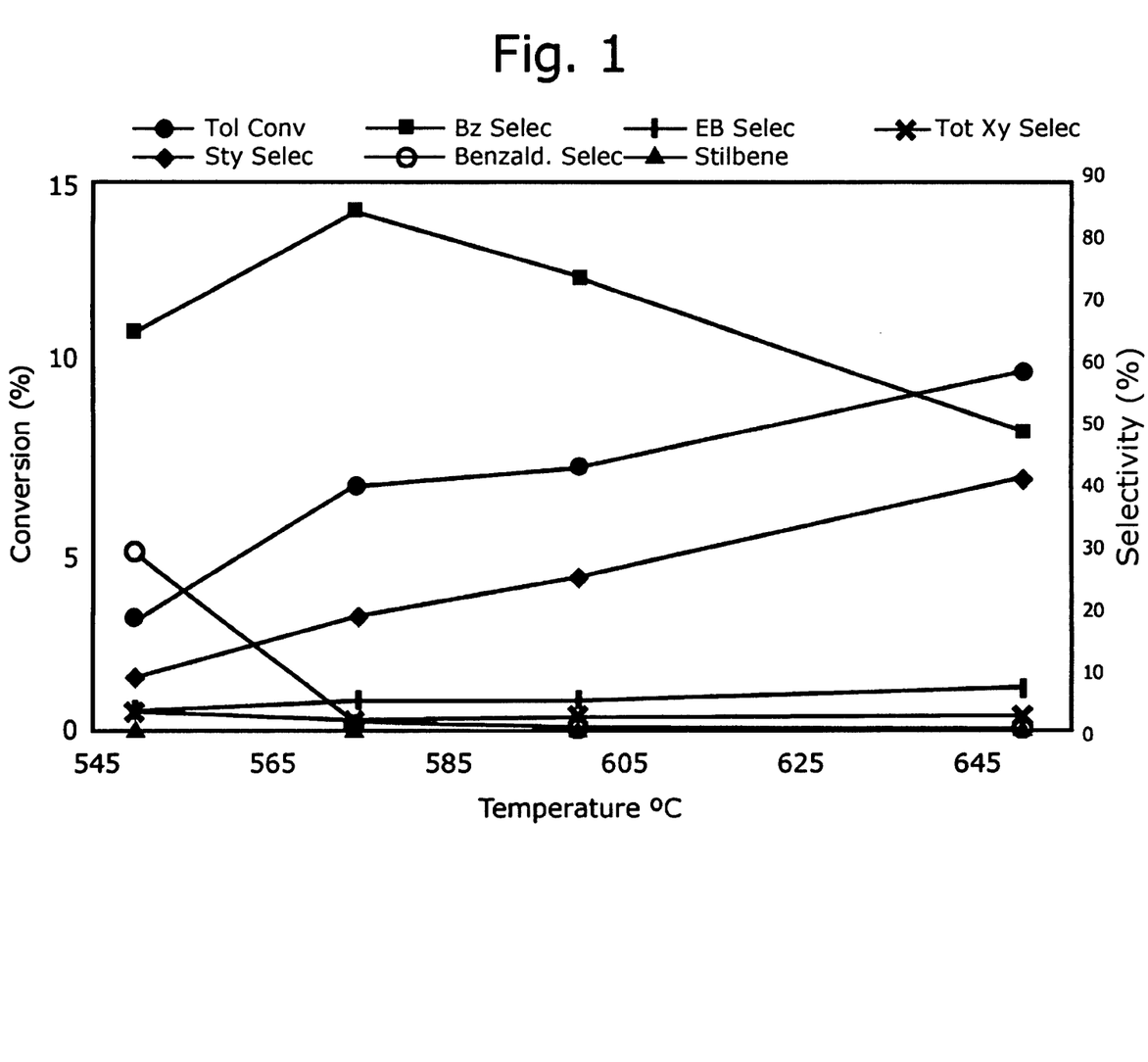
FIG. 1 is a graph displaying data, including conversion and selectivity, of OMT trials conducted in Comparative Example A.

The results are also shown in FIG. 1. FIG. 1 is a graphical representation of the data presented in Table 1. The x-axis shows temperature from 540° C. to 650° C. The y-axis on the left side of the graph corresponds to percent conversion of toluene. As can be seen, toluene conversion increased from 3% to 10% as temperature increased. The y-axis on the right side of the graph corresponds to percent selectivity for all of the products of the reactions. The products included benzene, ethylbenzene, xylene, styrene, benzaldehyde, and stilbene. Benzene was the product with the highest selectivity. However, its selectivity peaked at 570° C. and steadily decreased thereafter. Styrene, on the other hand, steadily increased with temperature. Because conversion and the selectivity of key products can vary with temperature, it may be possible to adjust product selectivity based on temperature. Benzene and styrene, for instance, can both be valuable products. The demands for these products may vary, and it can thus be useful to be able to control which of the two is the predominant product of OMT by adjusting the temperature. Selectivity of the other products was less variable. For benzaldehyde, the selectivity rapidly decreased from 30% to less than 1% at 575° C. Ethylbenzene selectivity, the total xylenes selectivity, and the stilbene selectivity remained low in all the trial runs.

COMPARATIVE EXAMPLE B

An oxidative catalyst was prepared comprising an oxide substrate, MgO, that was promoted with Li. The Li/MgO catalyst was used in the oxidative methylation of toluene. The catalyst included 2.5% Li by weight and was prepared from Lithium carbonate (13.69 g) salt (Sigma Aldrich, 98.0%) and MgO (16.304 g) (Fisher, 99%) by incipient wetness impregnation methodology in aqueous solution. The mixture was dried at 120° C. for 3 hours and then calcined at 850° C. in air for 1 hour. The catalyst was ground and sieved to 20-40 mesh size and 0.542 g of catalyst was loaded in a quartz reactor using quartz wool plugs and quartz chips to hold the catalyst bed in place. As a form of catalyst pretreatment, the reactor was heated to 850° C. under 100 ml/min of air and held for 2 hours. The reactor was then cooled down to 600° C. under helium to prepare for the OMT experiments.

For the oxidative methylation of toluene, the reaction temperature was 650° C., the oxygen source was air, the total flow of gasses was 335 cm$^3$/min (150 cm$^3$/min air, 150 cm$^3$/min methane, 0.167 cm$^3$/min liquid toluene), the methane to oxygen molar ratio was 5:1, and the methane to toluene molar ratio was 15:1. The reaction was performed twice, at two different space velocities. For the first trial, the space velocity was 37,085 cm$^3$g$^{-1}$h$^{-1}$. For the second trial, the space velocity was adjusted to 70,295 cm$^3$g$^{-1}$h$^{-1}$ by diluting the feed with nitrogen gas (150 cm$^3$/min air, 150 cm$^3$/min methane, 0.167 cm$^3$/min liquid toluene, 300 cm$^3$/min nitrogen). Space velocity is inversely related to residence time in the reactor, and modulation of space velocity influences the contact time between reactants and catalyst. At a higher space velocity, residence time and contact time are lower, and more reactants pass over the catalyst in a given period.

The results of the two OMT trials are shown in Table 2 below. Gas and liquid samples were analyzed for product distribution at twenty minutes.

TABLE 2

Results for OMT over Li/MgO catalyst

| Space Velocity (cm$^3$g$^{-1}$h$^{-1}$) | 37,085 | 70,295 |
|---|---|---|
| Methane Conversion (mol %) | 1.3 | — |
| Acetylene Selectivity (%) | 0.000 | 0.000 |
| CO$_2$ Selectivity (%) | 18.0 | 13.0 |
| Ethane Selectivity (%) | 0.0 | 0.3 |
| Ethylene Selectivity (%) | 0.0 | 0.0 |
| CO Selectivity (%) | 5.6 | 3.8 |
| Toluene Conversion (mol %) | 4.3 | 3.7 |
| Benzene Selectivity (%) | 58.6 | 58.3 |
| Ethylbenzene Selectivity (%) | 2.6 | 2.3 |
| Styrene Selectivity (%) | 9.9 | 10.4 |
| C$_8$ Selectivity (%) | 15.0 | 16.0 |
| Stilbene Selectivity (%) | 2.6 | 8.1 |

At the higher space velocity, there was greater selectivity to styrene (10.4% as compared to 9.9%). For toluene, the conversion dropped from 4.3% to 3.7%. The selectivity to benzene and ethylbenzene formation did not change with increasing space velocity. However, stilbene selectivity increased dramatically from 2.6 to 8.1 mol %.

EXAMPLE C

An oxidative catalyst was prepared comprising a MgO substrate that was promoted with Na, Cs, and Re. The Na/Cs/Re/MgO catalyst was used in the oxidative methylation of toluene. The catalyst included 5% Na by weight (3.811 g) of sodium chloride, 5% Cs by weight (2.199 g) of cesium nitrate, and 0.01% Re by weight (0.5856 g) of rhenium chloride and MgO (23.4033 g) (Fisher, 99%) by incipient wetness impregnation methodology in aqueous solution. The mixture was dried at 120° C. for 3 h and then calcined at 850° C. in air for 1 h. The catalyst was ground and sieved to 20-40 mesh size (420-841 μm) and 0.597 g of catalyst was loaded into a quartz reactor using quartz wool plugs and quartz chips to hold the catalyst bed in place. For catalyst pretreatment, the reactor was heated to 850° C. under 100 ml/min of air and held for 2 hours. The reactor was then cooled down to 600° C. under helium to prepare for the OMT experiments.

Five OMT trials were conducted, at reaction temperatures between 550° C. and 750° C. In all trials, the oxygen source was air, the total flow of gasses was 500 cm$^3$/min (244 cm$^3$/min methane, 240 cm$^3$/min air, 0.076 cm$^3$/min liquid toluene), the methane to oxygen molar ratio was 5:1, the methane to toluene molar ratio was 15:1, and the space velocity was 50,251 cm$^3$g$^{-1}$h$^{-1}$. Product samples were taken after the first twenty minutes of run time and analyzed for product distribution. The results of the trials are shown in the table below.

TABLE 3

Results for OMT over Na/Cs/Re/MgO

| | Temperature | | | | |
|---|---|---|---|---|---|
| | 550° C. | 600° C. | 650° C. | 700° C. | 750° C. |
| Toluene Conversion (%) | 1.7 | 1.9 | 3.3 | 12.1 | 39.9 |
| Benzene Selectivity (%) | 56.1 | 74.1 | 57.9 | 33.3 | 25.1 |
| Total Xylene Selectivity (%) | 3.6 | 3.3 | 3.4 | 2.9 | 1.9 |
| Stilbene Selectivity (%) | 3.3 | 0.9 | 0.5 | 0.2 | 0.2 |
| Benzaldehyde Selectivity (%) | 30.6 | 12.6 | 6.3 | 2.0 | 2.0 |
| Ethylbenzene Selectivity (%) | 3.7 | 5.0 | 8.4 | 8.6 | 4.5 |
| Styrene Selectivity (%) | 11.6 | 16.7 | 29.0 | 46.2 | 49.4 |

Figure 2:
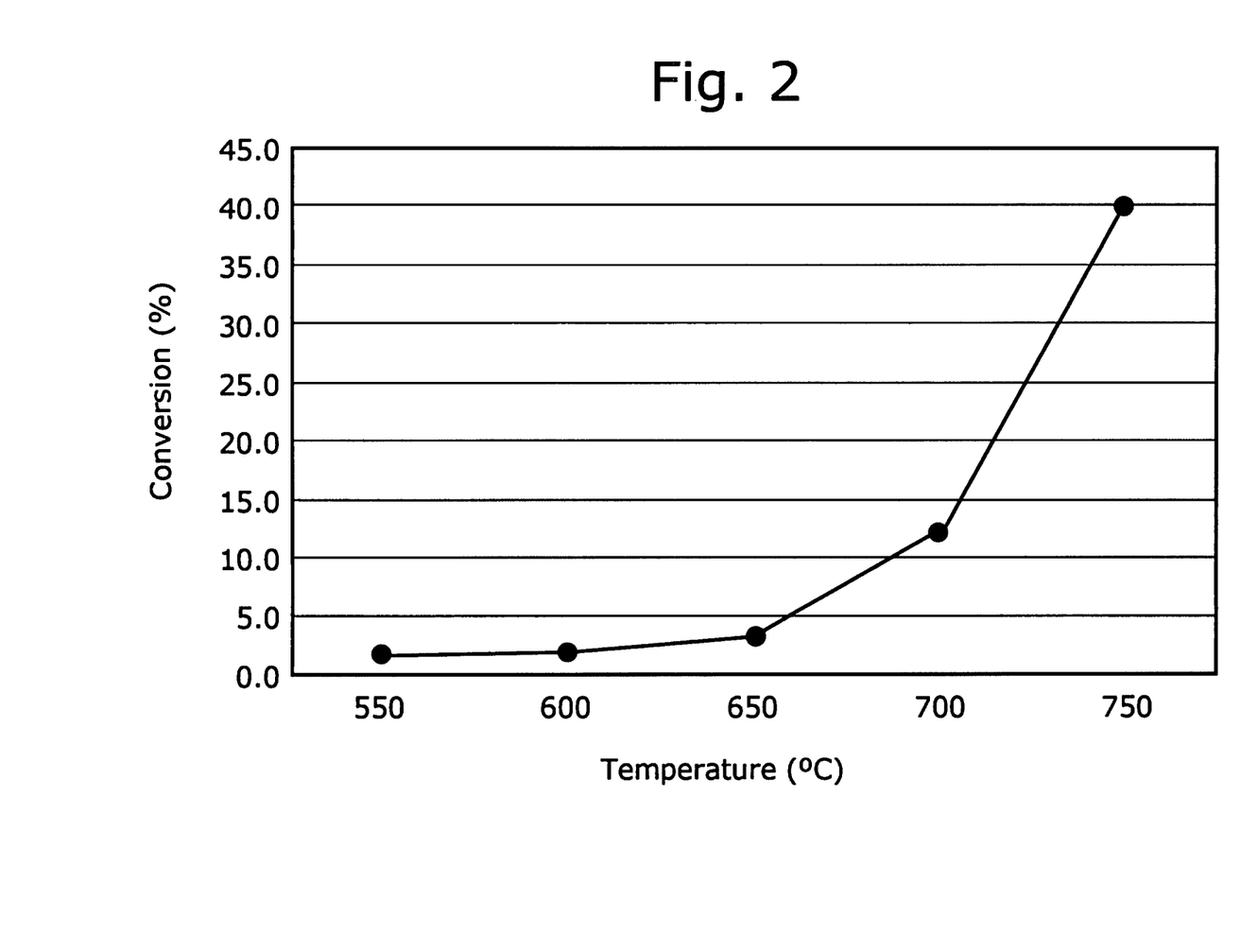
FIG. 2 is a chart showing the conversion of toluene over various temperatures, from the OMT trials conducted in Example C.
Figure 3:
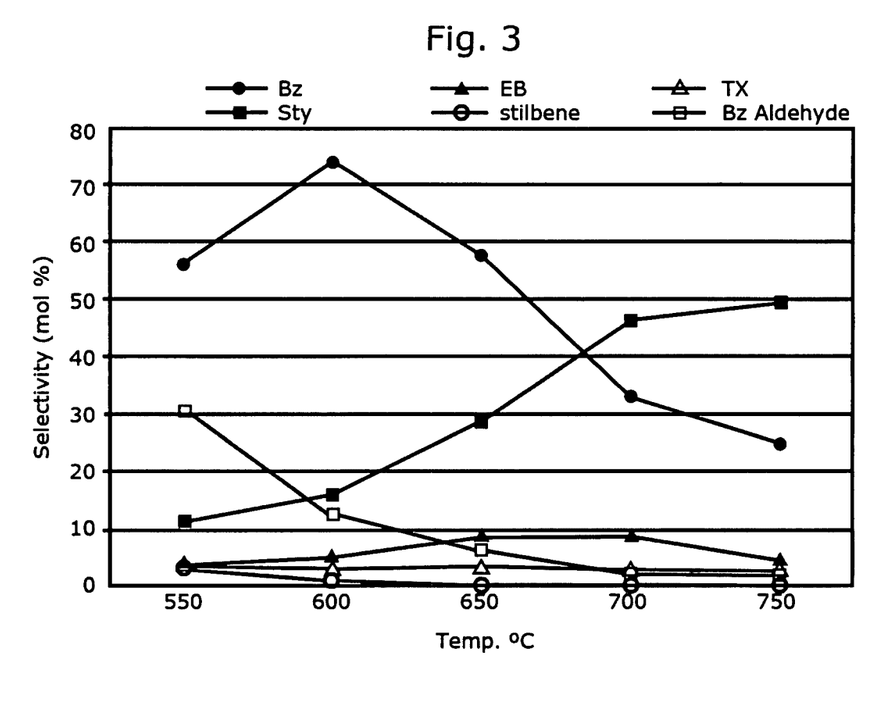
FIG. 3 is a chart showing the selectivity of various products obtained from the OMT trials conducted in Example C.

FIGS. 2 and 3 are graphical representations of the data shown in Table 3. FIG. 2 shows the data for toluene conversion, with temperature on the x-axis and percent conversion on the y-axis. The conversion of toluene increased from 1.7% at 550° C. to 39.9% at 750° C. FIG. 3 shows the data for selectivity. At temperatures from 550° C. to about 685° C., benzene is the predominant product, with selectivity above 50%. At around 685° C., the selectivity for benzene and that of styrene intersect and above 685° C., styrene is the predominant product. This approximate temperature of 685° C. also marks a transition in the rate of formation of styrene. The selectivity of styrene rises significantly from 550° C. to 685° C. (from 11.6% to 46.2%) and rises relatively little (from 46.2% to 49.4%) above 685° C.

The selectivity of the other products decreased or remained low over the temperatures explored. For instance, benzaldehyde selectivity decreased from 30.6% at 550° C. to 2.0% at 750° C.

Styrene is most commonly the desired product of OMT. However, depending on demand and process needs, other products can also be desired. Ethylbenzene, for instance, can be a desired product as the technology is well established for its conversion to styrene via dehydrogenation. It is thus a useful feature of this process that product distribution can be affected by modulation of reaction conditions such as temperature. Benzene was the product with the highest selectivity. However, its selectivity peaked at 600° C. and steadily decreased thereafter. Styrene, on the other hand, steadily increased with temperature. Because conversion and the selectivity of key products can vary with temperature, it may be possible to adjust product selectivity based on temperature. Benzene and styrene, for instance, can both be valuable products. The demands for these products may vary, and it can thus be useful to be able to control which of the two is the predominant product of OMT by adjusting the temperature.

EXAMPLE D

An oxidative catalyst was prepared comprising an oxide substrate, MgO, that was promoted with Ca and La. The Ca/La/MgO catalyst was used in the oxidative coupling of methane to toluene. The catalyst included 5% Ca by weight from Calcium oxide (2.10 g) and 5% La by weight from lanthanum oxide (3.51 g) and was prepared from calcium oxide salt, La$_2$O$_3$ (Sigma Aldrich, 98.0%) and MgO (24.38 g) (Fisher, 99%) by incipient wetness impregnation methodology in aqueous solution. The mixture was dried at 120° C. for 3 hours and then calcined at 850° C. in air for 1 hour. The catalyst was ground and sieved to 20-40 mesh size and 0.661 g of catalyst was loaded in a quartz reactor using quartz wool plugs and quartz chips to hold the catalyst bed in place. As a form of catalyst pretreatment, the reactor was heated to 850° C. under 100 ml/min of air and held for 2 hours. The reactor was then cooled down to 600° C. under helium to prepare for the OMT experiments.

Four OMT trials were conducted over the Ca/La/MgO catalyst at temperatures of from 550° C. to 700° C. Reactions conditions other than temperature were held constant. The oxygen source was air. The total flow of gasses was 498 cm$^3$/min (244 cm$^3$/min methane, 240 cm$^3$/min air, 0.067 cm$^3$/min liquid toluene). The methane to oxygen molar ratio was 5:1. The methane to toluene molar ratio was 15:1. The space velocity was 45,204 cm$^3$g$^{-1}$h$^{-1}$. The products were analyzed after twenty minutes for product distribution. The table below shows results for the four OMT trials.

TABLE 4

Results of OMT over Ca/La/MgO

| | Temperature | | | |
|---|---|---|---|---|
| | 550° C. | 600° C. | 650° C. | 750° C. |
| Toluene Conversion (%) | 3.0 | 5.8 | 7.5 | 12.6 |
| Benzene Selectivity (mol %) | 60.6 | 40.4 | 39.5 | 28.1 |
| Total Xylene Selectivity (mol %) | 5.0 | 4.6 | 4.1 | 3.5 |
| Stilbene Selectivity (mol %) | 0.3 | 0.2 | 0.4 | 0.0 |
| Benzaldehyde Selectivity (mol %) | 1.4 | 0.1 | 0.0 | 0.0 |
| Ethylbenzene Selectivity (mol %) | 5.9 | 5.7 | 5.2 | 4.5 |
| Styrene Selectivity (mol %) | 39.7 | 49.7 | 50.4 | 58.2 |

Figure 4:
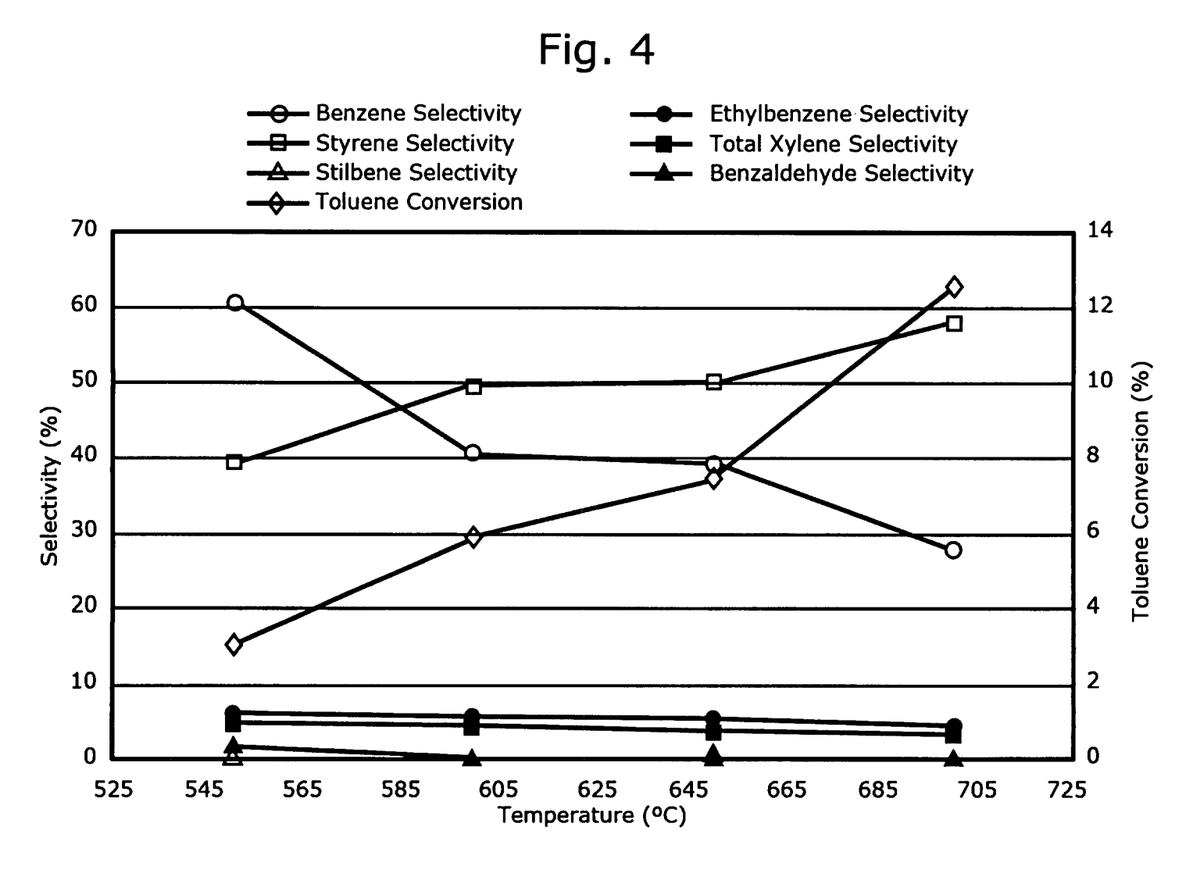
FIG. 4 is a chart showing data, including conversion and selectivity, of the OMT trials conducted in Example D.

FIG. 4 is a graphical representation of the data shown in Table 4. Toluene conversion increased with increasing temperature, going from about 3% conversion at 550° C. to nearly 13% conversion at 700° C. Product distribution also varied with temperature. Styrene increased in selectivity from about 40% at 550° C. to nearly 60% at 700° C. All other products had low selectivity and generally decreased in selectivity as the temperature rose.

EXAMPLE E

An oxidative catalyst was prepared comprising an oxide substrate, MgO, that was promoted with Sr and La. The Sr/La/MgO catalyst was used in the oxidative methylation of toluene. The catalyst included 5% Sr by weight from strontium nitrate (3.62 g) and 5% La by weight from lanthanum oxide (3.51 g) and was prepared from $Sr(NO_3)_2$ salt, $La_2O_3$ (Sigma Aldrich, 98.0%) and MgO (22.85 g) (Fisher, 99%) by incipient wetness impregnation methodology in aqueous solution. The mixture was dried at 120° C. for 3 hours and then calcined at 850° C. in air for 1 hour. The catalyst was ground and sieved to 20-40 mesh size and 0.855 g of catalyst was loaded in a quartz reactor using quartz wool plugs and quartz chips to hold the catalyst bed in place. As a form of catalyst pretreatment, the reactor was heated to 850° C. under 100 ml/min of air and held for 2 hours. The reactor was then cooled down to 600° C. under helium to prepare for the OMT experiments.

The Sr/La/MgO catalyst was used in four trials of OMT at temperatures from 500° C. to 650° C. All reaction conditions other than temperature were held constant during these trials. The oxygen source was air. The total flow of gasses was 498 $cm^3$/min (244 $cm^3$/min methane, 240 $cm^3$/min air, 0.067 $cm^3$/min liquid toluene). The methane to oxygen molar ratio was 5:1. The methane to toluene molar ratio was 15:1. The space velocity was 34,947 $cm^3 g^{-1} h^{-1}$. The products was sampled after 20 minutes and analyzed for product distribution. The table below shows the results of the four OMT trials.

TABLE 5

Results of OMT over Sr/La/MgO catalyst

| | Temperature | | | |
|---|---|---|---|---|
| | 500° C. | 550° C. | 600° C. | 650° C. |
| Toluene Conversion (mol %) | 0.4 | 1.1 | 6.1 | 15.8 |
| Benzene Selectivity (mol %) | 30.4 | 51.0 | 40.4 | 16.2 |
| Total Xylene Selectivity (mol %) | 15.8 | 6.7 | 3.9 | 2.5 |
| Stilbene Selectivity (mol %) | 1.3 | 0.2 | 0.2 | 0.3 |
| Benzaldehyde Selectivity (mol %) | 21.2 | 5.7 | 0.1 | 0.0 |
| Ethylbenzene Selectivity (mol %) | 5.2 | 6.6 | 7.5 | 4.5 |
| Styrene Selectivity (mol %) | 4.5 | 22.2 | 43.0 | 42.1 |

Figure 5:
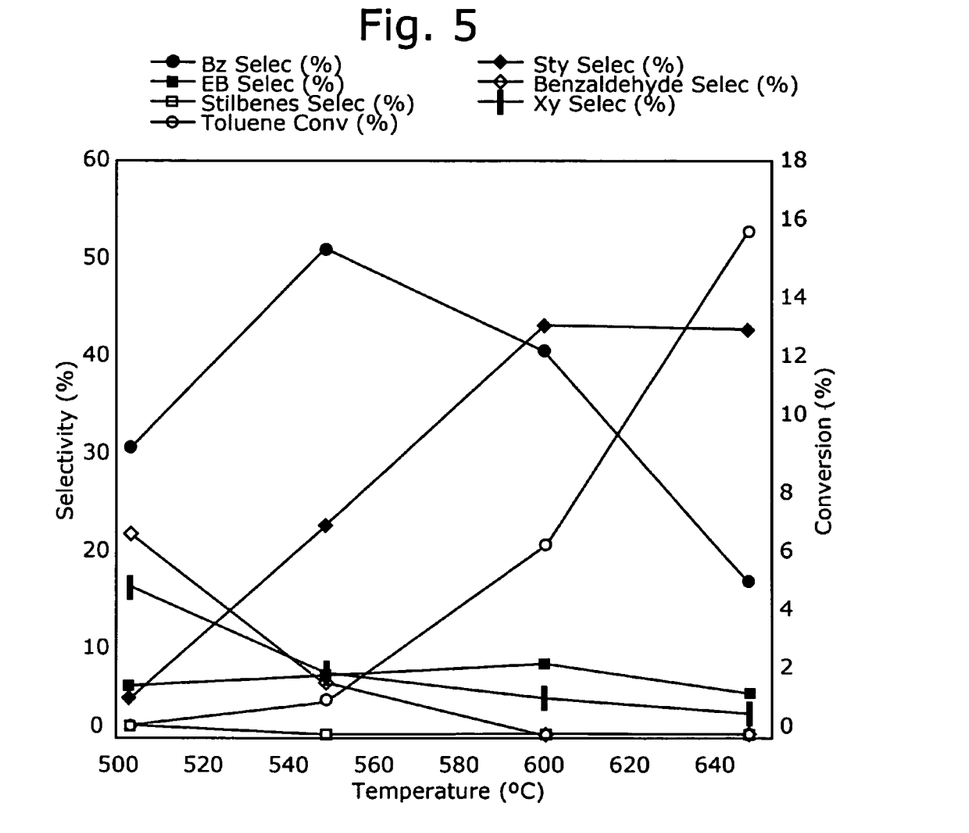
FIG. 5 is a chart showing data, including conversion and selectivity, of the OMT trials conducted in Example E.

FIG. 5 is a graphical representation of the data shown in Table 5. The toluene conversion increased with increasing temperature, from 0.4 mol % at 500° C. to 15.8 mol % at 650° C. Styrene selectivity also showed a general increase with increasing temperature, increasing from 4.5 mol % at 500° C. to 43.0 mol % at 600° C.

The benzene selectivity showed an initial increase in selectivity, with a peak of 51 mol % at 550° C. At temperatures above 550° C., however, benzene selectivity decreased down to 16.2 mol % at 650° C. At about 595° C., the benzene and styrene selectivity intersect at about 42.0 mol %. This temperature also seems to mark a change in the rate of formation of styrene. Below 595° C., styrene selectivity increased steadily with increasing temperature, but above this temperature styrene selectivity changed very little. All the products except benzene and styrene showed a general decrease in selectivity with increasing temperature.

Styrene is most commonly the desired product of OMT. However, depending on demand and process needs, other products can also be desired. Ethylbenzene, for instance, can be a desired product as the technology is well established for its conversion to styrene via dehydrogenation. It is thus a useful feature of this process that product distribution can be affected by modulation of reaction conditions such as temperature.

Figures are used herein to illustrate data, which are shown as data points on a graph. Lines connecting the data points are used to guide the eye and assist in illustrating general trends of the data. The lines are not intended as a predictor of where additional data points would necessarily fall, if they were available.

The term "$C_2$ selectivity" as used herein is the cumulative selectivity of acetylene, ethane, and ethylene.

The abbreviation of "OMT" as used herein refers to the oxidative methylation of toluene to form new compounds. For instance, toluene can couple with methane to form ethylbenzene and/or styrene.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

As used herein the space velocity shall be defined as: space velocity=[feed flow as vapor ($cm^3$/h)]/[catalyst weight (g)].

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A method for the oxidative coupling of methane and toluene comprising:
   providing a hydrocarbon feedstream comprising methane and toluene;
   providing an oxidative catalyst within a reactor, the catalyst consisting essentially of
   (A) Mg element from 40 to 90 wt. % of the catalyst;
   (B) at least one element selected from the group consisting of Cs and Re, wherein the elements from (B) comprise from 0.01 to 40 wt. % of the catalyst;
   (C) at least one element selected from the group consisting of Na, Sr, and Ca, wherein the elements from (C) comprise from 0.01 to 40 wt. % of the catalyst; and
   (D) oxygen, wherein oxygen comprises from 10 to 45 wt. % of the catalyst;
   feeding the hydrocarbon feedstream and an oxygen source to the reactor;
   carrying out oxidative coupling of methane to toluene over the oxidative catalyst according to an oxidative coupling condition; and
   recovering product hydrocarbons comprising ethyl benzene and styrene from the reactor.

2. The method of claim 1, wherein the oxidative coupling of methane to toluene occurs in the reactor with a molar ratio of methane to oxygen of from 1:1 to 100:1.

3. The method of claim 1, wherein the oxidative coupling of methane to toluene occurs in the reactor with a molar ratio of methane to toluene ranging from 1:1 to 50:1.

4. The method of claim 1, wherein the catalyst is pretreated before it is used for the oxidative coupling of hydrocarbons, the pretreatment comprising heating the catalyst to above 750° C.

5. The method of claim 1, wherein the composition of the product hydrocarbons can be adjusted by adjusting the temperature of the reaction.

6. The method of claim 1, wherein the composition of the product hydrocarbons can be adjusted by adjusting the space velocity of the reaction.

* * * * *